United States Patent
Van Rens et al.

(10) Patent No.: US 9,676,001 B2
(45) Date of Patent: Jun. 13, 2017

(54) DRIVER DEVICE AND DRIVING METHOD FOR DRIVING A LOAD, IN PARTICULAR AN ULTRASOUND TRANSDUCER

(71) Applicant: KONINKLIJKE PHILIPS N.V., Eindhoven (NL)

(72) Inventors: Antonia Cornelia Van Rens, Nuenen (NL); George Anthony Brock-Fisher, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 214 days.

(21) Appl. No.: 14/414,467

(22) PCT Filed: Jul. 11, 2013

(86) PCT No.: PCT/IB2013/055702
§ 371 (c)(1),
(2) Date: Jan. 13, 2015

(87) PCT Pub. No.: WO2014/013394
PCT Pub. Date: Jan. 23, 2014

(65) Prior Publication Data
US 2015/0174614 A1  Jun. 25, 2015

Related U.S. Application Data

(60) Provisional application No. 61/672,844, filed on Jul. 18, 2012.

(51) Int. Cl.
*B06B 1/02* (2006.01)
*A61B 8/00* (2006.01)
*A61B 8/12* (2006.01)

(52) U.S. Cl.
CPC .......... *B06B 1/023* (2013.01); *A61B 8/12* (2013.01); *A61B 8/445* (2013.01); *A61B 8/4483* (2013.01);
(Continued)

(58) Field of Classification Search
CPC . B06B 1/023; B06B 2201/20; B06B 2201/76; B06B 2201/51; A61B 8/445; A61B 8/4494; A61B 8/4483; A61B 8/12
See application file for complete search history.

(56) References Cited

U.S. PATENT DOCUMENTS

| | | | |
|---|---|---|---|
| 3,989,963 A | 11/1976 | Giaccardi | |
| 4,563,899 A * | 1/1986 | Nakamura | G10K 11/341 600/443 |

(Continued)

*Primary Examiner* — Daniel Pihulic

(57) ABSTRACT

The present invention relates to a driver device (40) for driving a load (52) having a plurality of separate capacitive load elements (52), in particular an ultrasound transducer having a plurality of transducer elements (52), comprising: input terminals (44, 46) for connecting the driver device (40) to power supply (48); a plurality of output terminals (50) each for connecting the driver device (40) to one of load elements (52), a first controllable switch (54) connected to a first of the input terminals (44), and a plurality of driving elements (42) each having a second controllable switch (60) and a resistor (58) connected in series to each other, wherein each of the driving elements (42) is connected in series with the first controllable switch (54) and to a second of the input terminals (46), and wherein each of the output terminals (50) is connected to one of the driving elements (42) for powering the load elements (52).

13 Claims, 4 Drawing Sheets

(52) U.S. Cl.
CPC ........ *A61B 8/4494* (2013.01); *B06B 2201/20* (2013.01); *B06B 2201/51* (2013.01); *B06B 2201/76* (2013.01)

(56) References Cited

U.S. PATENT DOCUMENTS

| | | | |
|---|---|---|---|
| 4,817,066 A * | 3/1989 | Takasugi | G01S 7/52017 367/105 |
| 4,841,492 A | 6/1989 | Russell | |
| 5,724,312 A | 3/1998 | Oppelt | |
| 7,314,445 B2 * | 1/2008 | Wodnicki | H04B 11/00 310/317 |
| 7,728,487 B2 * | 6/2010 | Adachi | A61B 8/4483 310/309 |
| 7,824,335 B2 * | 11/2010 | Wodnicki | A61B 8/00 600/437 |
| 7,859,941 B2 | 12/2010 | Freeman et al. | |
| 7,878,064 B2 * | 2/2011 | Abbott | G01N 29/022 73/590 |
| 7,982,362 B2 * | 7/2011 | Adachi | A61B 8/4483 310/309 |
| 8,721,550 B2 * | 5/2014 | Oguzman | A61B 8/4483 600/459 |
| 9,022,941 B2 * | 5/2015 | Hatayama | B06B 1/0207 340/870.18 |
| 2005/0154300 A1 * | 7/2005 | Wodnicki | H04B 11/00 600/437 |
| 2006/0264747 A1 | 11/2006 | Freeman et al. | |
| 2009/0001853 A1 * | 1/2009 | Adachi | A61B 8/4483 310/323.19 |
| 2009/0182229 A1 | 7/2009 | Wodnicki | |
| 2010/0201222 A1 * | 8/2010 | Adachi | A61B 8/4483 310/317 |
| 2015/0174614 A1 * | 6/2015 | Van Rens | B06B 1/023 600/466 |

* cited by examiner

DRIVER DEVICE AND DRIVING METHOD FOR DRIVING A LOAD, IN PARTICULAR AN ULTRASOUND TRANSDUCER

This application is the U.S. National Phase application under 35 U.S.C. §371 of International Application No. PCT/IB2013/055702, filed on Jul. 11, 2013, which claims the benefit of U.S. Provisional Application No. 61/672,844 filed on Jul. 18, 2012. These applications are hereby incorporated by reference herein.

FIELD OF THE INVENTION

The present invention relates to a driver device and a corresponding driving method for driving a load having a plurality of separate capacitive load elements, in particular an ultrasound transducer comprising a plurality of transducer elements. Further, the present invention relates to an ultrasound apparatus.

BACKGROUND OF THE INVENTION

In the field of ultrasound transducer for three-dimensional imaging transducer probes are designed by integrating a two-dimensional array of acoustic transducer elements. The transducer elements are typically formed of piezoelectric materials for emitting pressure waves. The transducer elements are usually also used to detect ultrasound reflections for three-dimensional imaging. The transducer elements are typically controlled or driven by ASICs having integrated driver elements for driving the transducer elements separately.

The existing 3D ultrasound transducers are used for transcutaneous and transesophageal imaging and provide an imaging frequency in the range of 2 to 10 MHz. In this imaging frequency range, the ASICs for driving the transducer elements are designed to have a circuitry to control, transmit and receive the acoustic signal in an array that corresponds to the array of a single transducer element. The size of the transducer elements is determined by the imaging requirements of the certain application, i.e. the frequency and the field of view of the ultrasound transducer. Typically a pitch of the transducer elements in a two-dimensional array is between 100 and 300 μm.

For catheter-based imaging devices and systems the currently available imaging transducer probes and driver devices are too large and operate at two low frequencies for providing a necessary two-dimensional and three-dimensional imaging inside the organs, e.g. inside the heart. In particular for applications to examine the heart, the transducer probes have to provide guidance and location information for ablation procedures and structural heart repairs. Those applications need higher frequencies, e.g. 15-60 MHz in order to provide the required imaging characteristics. Further, to achieve the frequency and size requirements of the catheter-based application, Capacitive Micromachined Ultrasound Transducers (CMUTs) can be employed replacing the piezoelectric transducer elements. The CMUTs can provide reasonable acoustic performance at higher frequencies and smaller dimensions than the piezoelectric material and can be manufactured using cheap semiconductor processing techniques.

A possibility to reduce the dimensions of the driver device is known from US 2006/0264747 A1. The microbeam former channels of this driver device are combined to clusters having a common voltage source or common current source. However, due to the large amount of high voltage transistors being integrated in the ASICs the size of the driver device is still too large to be accommodated in a catheter-based transducer probe.

SUMMARY OF THE INVENTION

It is therefore an object of the present invention to provide an improved driver device having a reduced size and a corresponding driving method for driving a load having a plurality of separate capacitive load elements.

According to one aspect of the present invention a driver device for driving a load having a plurality of separate capacitive load elements, in particular an ultrasound transducer having a plurality of transducer elements is provided, comprising:
  input terminals for connecting a driver device to a power supply;
  a plurality of output terminals connecting the driver device to one of the load elements,
  a first controllable switch connected to a first of the input terminals and
  a plurality of driving elements each having a second controllable switch and a resistor connected in series to each other, wherein each of the driving elements is connected in series with the first controllable switch and to a second of the input terminals, and wherein each of the output terminals is connected to one of the driving elements for driving the load elements.

According to another aspect of the present invention, a driving method for driving a load having a plurality of separate capacitive load elements, in particular for driving an ultrasound transducer having a plurality of transducer elements is provided, comprising the steps of:
  connecting the load elements to a driver device,
  connecting the capacitive load elements to a first voltage level via a single controllable switch, and
  connecting the capacitive load elements individually to a second voltage level via a plurality of controllable switches each associated to one of the capacitive load elements.

According to still another aspect of the present invention an ultrasound apparatus is provided comprising an ultrasound transducer having a plurality of transducer elements, in particular an array of transducer elements, and at least one driver device for individually driving the ultrasound transducer elements as provided according to the present invention.

Preferred embodiments of the invention are defined in the dependent claims. It shall be understood that the claimed method has similar and/or identical preferred embodiments as the claimed device and as defined in the dependent claims.

The present invention is based on the idea to charge or discharge the capacitive load via a single high voltage transistor and to individually discharge or charge the capacitive load elements by means of second high voltage transistors individually associated to the output terminals. Since all of the capacitive load elements are charged or discharged via the single high voltage transistor, the overall amount of integrated transistor elements can be reduced. Hence, by means of the driver device according to the present invention and the driving method, the size of the driver device can be significantly reduced.

In a preferred embodiment, the output terminals are each connected to a node between the resistor and the second controllable switch. By means of this special connection, the capacitive load elements are separated from each other by means of the resistors that the capacitive load element can be charged slowly and easily individually discharged without interfering with each other and without causing acoustic energy.

In a further embodiment, the driver device comprises a plurality of switch control elements associated to each of the second controllable switches for controlling the second controllable switches. The switch control elements are provided to control the second controllable switches individually to charge or discharge the capacitive load elements individually.

In a further embodiment, the first controllable switch is provided for charging the capacitive load elements and wherein the second controllable switches are provided for individually discharging the capacitive load elements. This is a simple solution to drive the ultrasound transducer elements individually with low control effort and to provide a two- or three-dimensional pressure wave.

In a further embodiment, the second controllable switches are provided for charging the capacitive load elements individually and the first controllable switch is provided for discharging the capacitive load elements. This is a simple solution to drive the ultrasound transducer elements individually with low control effort and to provide a two- or three-dimensional pressure wave.

In a further embodiment, the switch control elements are adapted to switch the second controllable switches on a staggered time basis. This is a practical solution to provide a three-dimensional pressure pulse for high quality three-dimensional imaging.

In a further embodiment, the switch control elements are adapted to control the first and the second controllable switches such that the first and the second controllable switches are at least temporarily simultaneously conductive. This minimizes cross-talk between the driving elements.

In a further embodiment each of the driving elements has a receiving circuitry connected to the second controllable switch. This is a possibility to drive the capacitive load element and to detect ultrasound reflections by means of the driving elements to further reduce the size of the driver device.

In a further embodiment each of the second controllable switches are connected via a third controllable switch to the second input terminal and wherein each of the receiving circuitries is connected to a node between each of the second controllable switches and each of the third controllable switches. This is a simple solution to connect and disconnect the receiving circuitry and the capacitive load elements to detect the ultrasound reflections to activate and deactivate the receiving circuitries.

In a further embodiment, the switch control elements are adapted to switch the third controllable switches and the second controllable switches in a drive mode of the driver device in a conductive state. This is a practical possibility to activate a drive mode of the driver device with low control effort.

In a further embodiment, the switch control elements are adapted to switch the second controllable switches in a conductive state and the third controllable switches in a non-conductive state in a receive mode when the receiving circuitry is activated. This is a useful solution to switch from the drive mode of the driver device to the receiving mode of the driver device with low control effort.

In a further embodiment, the first controllable switches and the second controllable switches are integrated in one single semiconductor device. This is a solution to provide a small driver device for catheter-based imaging ultrasound transducers.

As mentioned above, the present invention provides a driver device for driving a plurality of separate capacitive load elements such as transducer elements for three-dimensional ultrasound imaging, wherein the separate capacitive load elements can be driven individually and wherein the size of the driver device is reduced. The reduction of the dimensions of the driver device is achieved since the capacitive load elements are all charged in one step via the first controllable switch and individually discharged by means of the second controllable switches. Hence, the amount of switches and the size of the driver device can be reduced.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
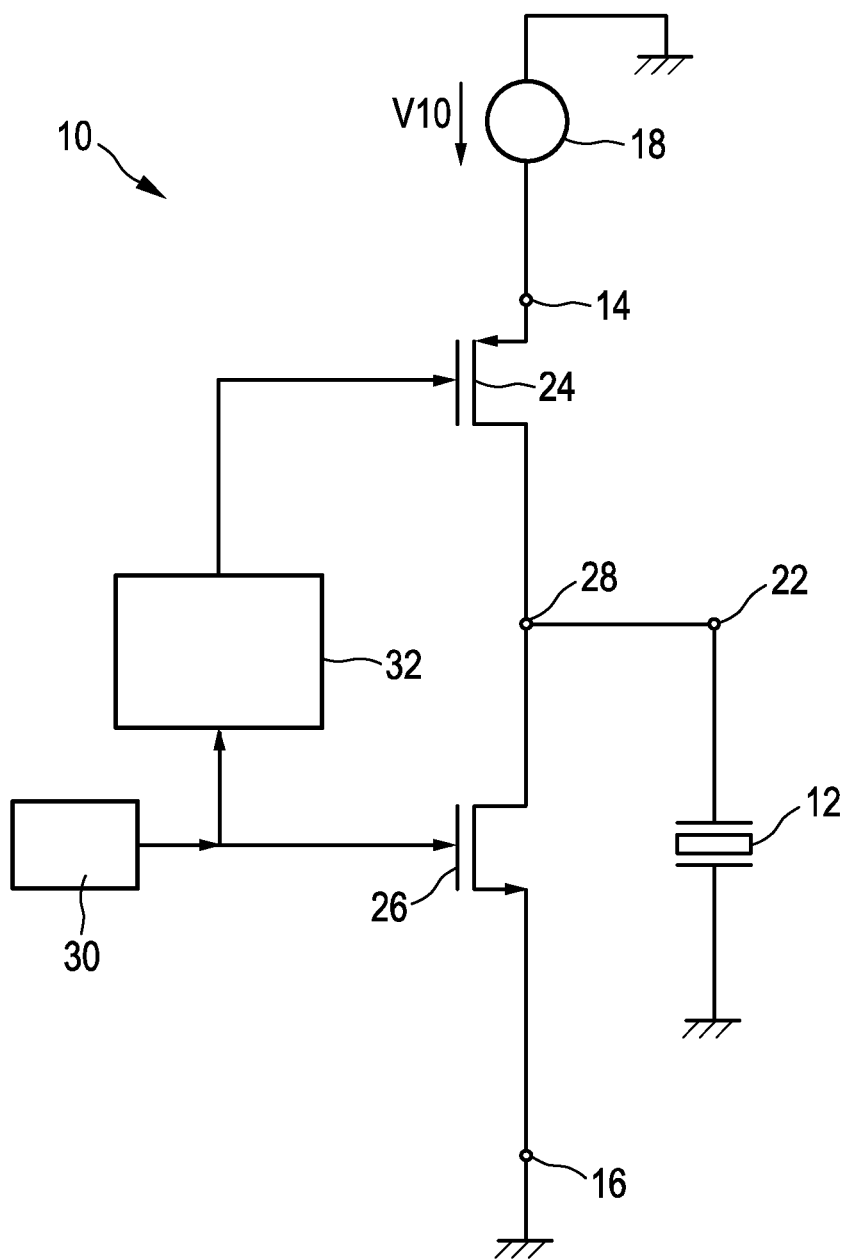
FIG. 1 shows a schematic block diagram of a known driver device for driving a transducer element of an ultrasound transducer.

FIG. 1 shows a known driver device 10 for driving ultrasound transducer elements 12. The driver device 10 comprises input terminals 14, 16 as supply connections for connecting the driver device 10 to a power source 18, which provides a supply voltage V10 to the driver device 10. In this certain embodiment, the second input terminal 16 and the power source 18 are each connected to a ground level 20.

The driver device 10 comprises an output terminal 22, for connecting the driver device 10 to an ultrasound transducer element 12. The driver device 10 comprises two controllable switches 24, 26 connected in series to each other, wherein the output terminal 22 is connected to a node 28 between the first and the two controllable switches 24, 26. The controllable switches 24, 26 form a half bridge for providing different voltage levels to the output terminal 22. The controllable switches 24, 26 are connected via a control input to a control unit. The control unit 30 controls the controllable switches 24, 26 by means of a control signal and are switched in an alternating fashion by means of a level shifter 32 connected between the control unit 30 and the first controllable switch 24.

By providing the different voltage levels, in this case V10 and ground to the ultrasound transducer element 12, the ultrasound transducer element 12 is charged and discharged in an alternating fashion and provides a pressure wave having a frequency corresponding to the switching frequency of the control signal and of the controllable switches 24, 26.

The controllable switches 24, 26 are formed as high voltage semiconductor transistors having different conductivity types. The high voltage transistors are typically integrated in a semiconductor device such as an ASIC to reduce the dimensions of the driver device 10. For driving a plurality of transducer elements 12 such as an array of transducer elements, a corresponding amount of driver devices 10 have to be integrated in one ASIC and need to be isolated from each other such that the chip area of those ASICs is typically large.

Figure 2:
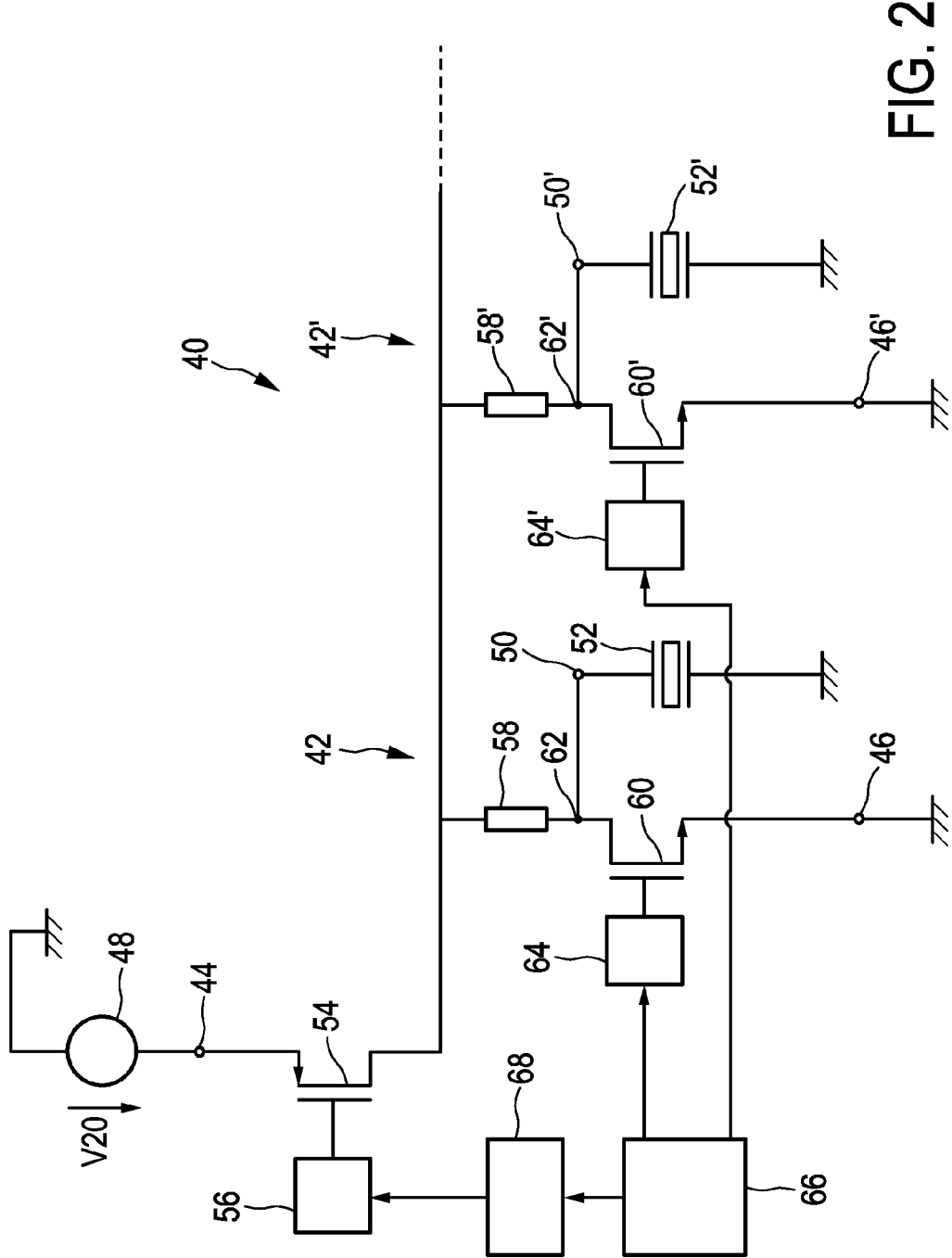
FIG. 2 shows a driver device having a plurality of driving elements for individually driving separate transducer elements.

FIG. 2 shows a schematic block diagram of a driver device for driving a plurality of transducer elements generally denoted by 40. The driver device 40 comprises a plurality of driving elements 42, 42'. In FIG. 2 as an example two driving elements 42, 42' are shown, however, the driver device 40 comprises typically more than two driving elements 42, 42' such as e.g. 36 driving elements, corresponding to the amount of transducer elements to be driven within one patch of transducer elements. The complete transducer probe contains many transducer patches and e.g. 1000 transducer elements. The transducer elements are preferably arranged in patches of about e.g. 6×6 elements to achieve an optimum of the area utilization, which is reduced for small amounts of transducer elements in one patch and the power loss, which is increased for large patches due to the overlap time of the first and the second controllable switches. The driver device 40 comprises input terminals 44, 46 as supply connections for connecting the driver device to a power source 48, which provides a supply voltage V20 for driving the driver device 40. In this case, the second input terminal 46, 46' and the power source 40 are each connected to ground, however, in a certain embodiment, the input terminal 46, 46' can also be connected to a different voltage level.

The driving elements 42, 42' are each connected to an output terminal 50, 50' for individually driving the transducer elements 52, 52'. The transducer elements 52, 52' are typically integrated in a one- or two-dimensional array of transducer elements to form an ultrasound transducer and to provide two- or three-dimensional pressure waves.

The driver device 40 comprises a first controllable switch 54 connected to a first of the input terminals 44 and which is controlled by a switch control unit 56. The driving elements 42, 42' are each connected to the first controllable switch 54. The driving elements 42, 42' are connected in parallel to each other and each comprises a resistor 58 and a second controllable switch 60, which are connected in series between the first controllable switch 54 and the second output terminal 46. A node 62, 62' between the resistor 58, 58' and the second controllable switch 60, 60' is connected to the respective output terminal 50, 50' of the driving elements 42, 42' to provide an output voltage to each of the transducer elements 52, 52'. The second controllable switches 60, 60' are each controlled via a control signal provided by a switch control unit 64, 64'. The driver device 40 comprises a control unit 66, which controls the switch control units 56, 64, 64' for switching the first controllable switch 54 and the second controllable switches 60, 60'. A level shifter 68 is connected between the control unit 66 and the switch control unit 56 of the first controllable switch 54 to switch the first controllable switch 54 and the second controllable switches 60, 60'.

During operation of the driver device 40, the first controllable switch 54 is switched on i.e. to a conductive state while the second controllable switches 60, 60' are switched off i.e. in a non-conductive state. During this on-time of the first controllable switch 54, the output terminals 50, 50' are connected via the resistor 58, 58' to the power supply 48. During this on-time, the capacitive load elements 42, 42', i.e. the transducer elements 52, 52' are charged via the resistor 58, 58'. After the transducer elements 52, 52' have been charged to the voltage V20, the second controllable switches 60, 60' are individually switched on to discharge the capacitive load elements 42, 42', i.e. the transducer elements 42, 42' individually by connecting the output terminals 50, 50' to the second input terminal 46. The first controllable switch 54 may be switched off before the second controllable switches 60, 60' are switched on or at the same time when the second controllable switches 60, 60' are switched on to reduce the power loss in the resistor 58, 58'. Alternatively, the first controllable switch 54 may be still conductive when the second controllable switches 60, 60' are switched on to the conductive state to reduce cross-talk between the transducer elements 52, 52'. Due to the capacity of the transducer elements 52, 52' and the resistor 58, 58', the charging of the transducer elements 52, 52' is performed simultaneously via the first controllable switch 54 and comparatively slow. Due to the low frequency of the charging no significant acoustic pressure is created by the transducer elements 52, 52'. During the fast discharging the transducer elements 52, 52' a pressure wave is individually created by each of the transducer elements 52, 52'.

The driving elements 42, 42' form different channels of the driver device 40, wherein each channel contains the individual switch control units 64, 64' to activate the second controllable switches 60, 60'. Dependent on the timing of the switching of the second controllable switches 60, 60' the pressure wave emitted by the ultrasound transducer can be steered and focused in a traditional manner.

The first controllable switch 54 and the second controllable switches 60, 60' are high voltage transistors having different conductivity types. In the case shown in FIG. 2, the first controllable switch 54 is a p-MOS transistor and the second controllable switches are n-MOS transistors. In an alternative embodiment the conductivity types can be vice versa.

Typically the transducer elements 52, 52' are integrated together with the driver device 40 and located close together. Therefore, the different channels can be activated with short timing delays relative to each other. The control of the first controllable switch 54 can be optimized with respect to the control of the second controllable switches 60, 60'. An overlap of the on-time of the first controllable switch 54 and the second controllable switches 60, 60' should be minimized or optimized. In a certain embodiment, the first controllable switch 54 is switched on during the switches of the second controllable switches to minimize the cross-talk between the different driving elements 42, 42'. The timing of the level shifter 68 is not critical as in the driver device 10 shown in FIG. 1, since the resistors 58, 58' prevent the driver device 40 from a short circuit. Hence, the level shifter 68 may be a simple circuit, which is not timing-critical.

In an alternative embodiment, the input terminal 44 is connected to ground and the input terminals 46, 46' are connected to the power source 48 and the transducer elements 50, 50' are individually charged via the second controllable switches 60, 60' and discharged via the first controllable switch 54.

Figure 3:
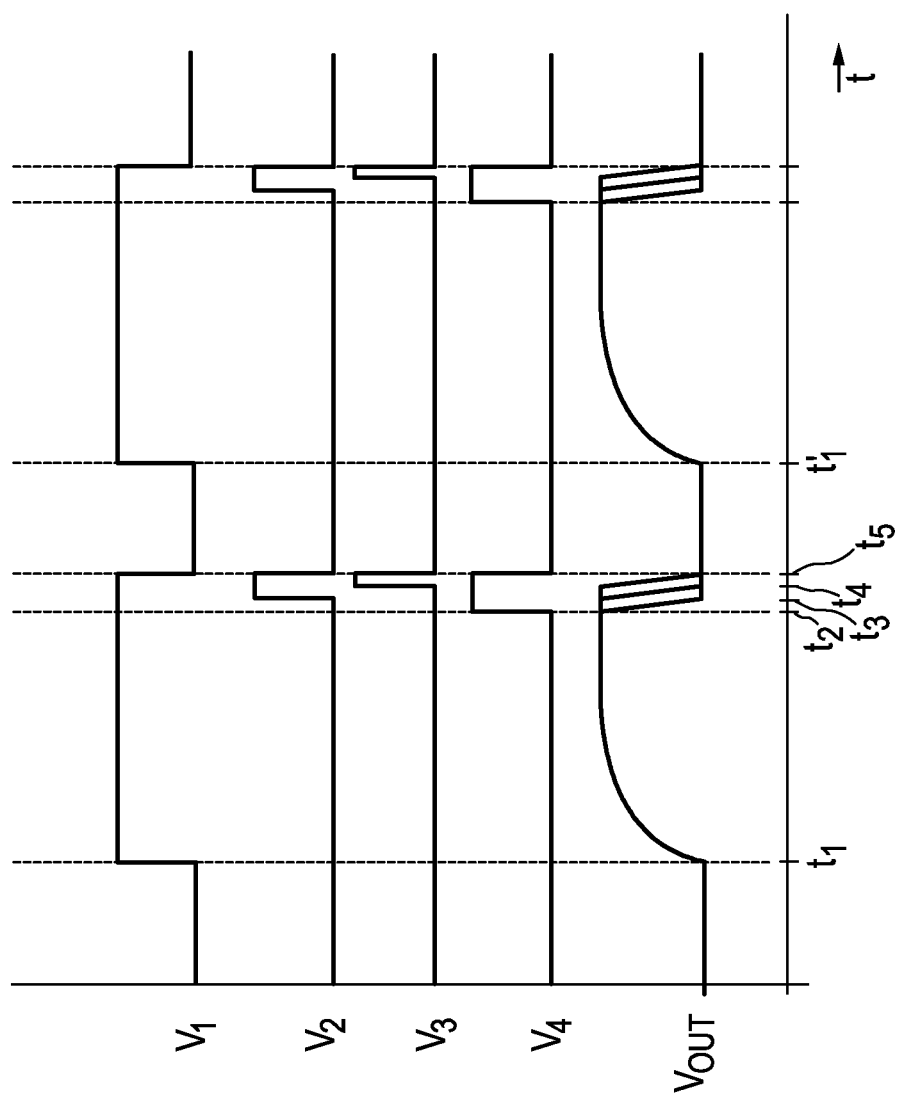
FIG. 3 shows a timing diagram of the controllable switches of the driver device shown in FIG. 2 and the output voltage for powering the transducer elements.

FIG. 3 shows a timing diagram of the driver device 40 having three driving elements 42 for driving three transducer elements.

In FIG. 3 a drive signal V1 for driving the first controllable switch 54 is shown schematically and three drive signals V2, V3, V4 are shown schematically for driving the second controllable switches 60 of three different driving elements 42. Further, an output voltage $V_{out}$ of the different output terminals 50 of the three driving elements 42 is shown schematically.

At t1 the first controllable switch 54 is switched on i.e. to a conductive state while the second controllable switches 60 are switched off i.e. in a non-conductive state. The voltage $V_{out}$ increases slowly while the transducer elements 52 are simultaneously charged. At t2 one of the second transistors 60 is switched on as shown by the driving signal V4. At t2 the respective transducer element 52 associated to this second transistor is discharged rapidly as shown by rapid decrease of the output voltage $V_{out}$ at t2. At t3 a second of the second controllable switches is switched on as shown by the respective driving signal V2 and the associated transducer element 52 is discharged as shown by the rapid decrease of output voltage $V_{out}$ at t3. At t4, a third of the second controllable switches is switched on as shown by the respective drive signal V3 and the associated transducer element 52 is discharged as schematically shown by the output voltage $V_{out}$. At t5 the first controllable switch 54 and the three second controllable switches 60 are switched off. During the phase between t2 and t5 the pressure wave of the ultrasound transducer is generated. At t5 all controllable switches 54, 60 are switched off and the driver device 40 is switched in a read-mode. During the read-mode, the transducer elements 52 detect ultrasound reflections which cause a reflection current in the transducer elements 52 which can be detected by the driver device 40 as described in the following. At t1', the charging of the transducer elements 52 starts again. In this embodiment, at t5 the second controllable switches 60 are switched off for the following receive mode, however, depending on the receiving circuitry to detect the current of the ultrasound transducer elements 52, the second controllable switch 60 may alternatively remain switched on during the receive mode.

Figure 4:
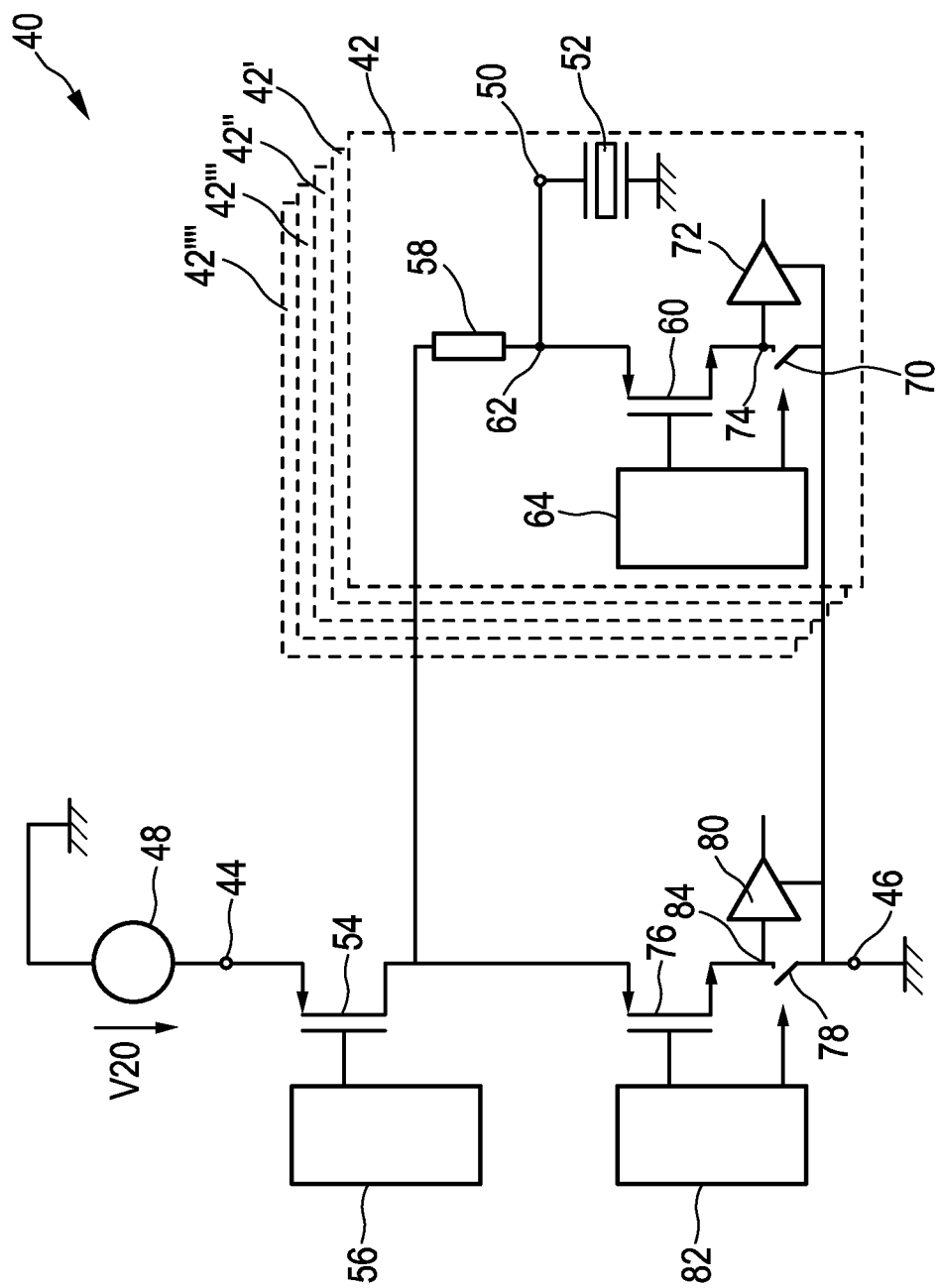
FIG. 4 shows a schematic block diagram of a driver device for driving transducer elements and for measuring ultrasound reflections by the transducer element.

FIG. 4 shows an embodiment of the driver device 40 including receiving elements for detecting ultrasound reflections of the transducer elements 52. Identical elements are denoted by identical reference numerals, wherein here merely the differences are explained in detail.

The driver device 40 shown in FIG. 4 comprises five detection elements 42, 42', 42", 42"', 42"", wherein merely one of the driving elements 42 is shown in detail and the other driving elements 42', 42", 42"', 42"" are schematically shown.

A third controllable switch 70 is connected between the second controllable switch 60 and the second input terminal 46. A receiving circuitry 72 is connected to a node 74 between the second controllable switch 60 and the third controllable switch 70. The switch control unit 64 is connected to the third controllable switch 70 for controlling the third controllable switch 70. The third controllable switch 70 is preferably a low-voltage transistor.

In a driving mode of the driver device 40 between t2 and t5 shown in FIG. 3 the third controllable switch 70 of each driving element 42 is switched on to a conductive state, the receiver circuitry 72 is turned off and the second controllable switch 60, 60' is switched on to a conductive state to generate the acoustic pressure. The second controllable switch 60, 60' in the drive mode behave as a cascading stage and prevents the node 74 from high voltage so that the receiver circuitry 72 can be formed of low voltage components. During this drive mode the acoustic pressure waves are provided as described above. During a receive mode between t5 and t1' as shown in FIG. 3, the second controllable switch 60, 60' remains conductive and the third controllable switch 70 is switched off to a non-conductive state. The receiver circuitry 72 is activated and the current generated by the transducer elements 52 flows via the second controllable switch 60 into the receiver circuitry 72 to detect the transducer current and to detect the respective ultrasound reflections. The receiver circuitry 72 may function in this case as a transimpedance amplifier with a low input impedance. Hence, the driver device 40 shown in FIG. 4 can drive the transducer element 52 for providing a focused pressure wave and can also detect the ultrasound reflection.

In a further embodiment, the driver device 40 comprises one fourth controllable switch 76, one fifth controllable switch 78 and a second receiver circuitry 80 associated to the first controllable switch 54. The fourth controllable switch 76 and the fifth controllable switch 78 are controlled by means of a switch control unit 82. The fourth controllable switch 76 and the fifth controllable switch 78 are connected in series between the first controllable switch 54 and the second input terminal 46. The second receiving circuitry 80 is connected to a node 84 between the fourth controllable switch 76 and the fifth controllable switch 78. The second receiving circuitry 80 is activated in the receive mode of the driver device 40 and causes a low impedance which minimizes cross-talk between the driving elements 42, 42', 42", 42"', 42"" further.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A driver device for driving a plurality of separate capacitive load elements, the device comprising:
   first and second input terminals for connecting the driver device to a power supply;
   a plurality of output terminals each connecting the driver device to separate capacitive load elements;
   a first controllable switch connected to the first input terminal; and
   a plurality of driving elements each having a second controllable switch and a resistor connected in series to each other, wherein each of the driving elements is connected in series with the first controllable switch and to the second input terminal, and wherein each of the output terminals is connected to one of the driving elements for powering the load elements,
   wherein each of the capacitive load elements is charged via a first electrical path and discharged via a second electrical path different than the first electrical path.

2. The driver device as claimed in claim 1, wherein the output terminals are each connected to a node between the resistor and the second controllable switch.

3. The driver device as claimed in claim 1, further comprising a plurality of switch control elements associated to each of the controllable switches for controlling the controllable switches.

4. The driver device as claimed in claim 1, wherein the first controllable switch is configured to charge the capacitive load elements and wherein the second controllable switches are configured to individually discharge the capacitive load elements.

5. A driver device for driving a plurality of separate capacitive load elements, the device comprising:
   first and second input terminals for connecting the driver device to a power supply;
   a plurality of output terminals each connecting the driver device to separate capacitive load elements;
   a first controllable switch connected to the first input terminal; and
   a plurality of driving elements each having a second controllable switch and a resistor connected in series to each other, wherein each of the driving elements is connected in series with the first controllable switch and to the second input terminal, and wherein each of the output terminals is connected to one of the driving elements for powering the load elements,
   wherein the first controllable switch is configured to discharge the capacitive load elements and wherein the second controllable switches are configured to individually charge the capacitive load elements.

6. The driver device as claimed in claim 5, comprising switch control elements adapted to switch the second controllable switches on a staggered time basis.

7. A driver device for driving a plurality of separate capacitive load elements, the device comprising:
   first and second input terminals for connecting the driver device to a power supply;
   a plurality of output terminals each connecting the driver device to separate capacitive load elements;
   a first controllable switch connected to the first input terminal;
   a plurality of driving elements each having a second controllable switch and a resistor connected in series to each other, wherein each of the driving elements is connected in series with the first controllable switch and to the second input terminal, and wherein each of the output terminals is connected to one of the driving elements for powering the load elements; and
   switch control elements adapted to control the first and the second controllable switches such that the first and the second controllable switches are temporarily simultaneously conductive.

8. The driver device as claimed in claim 1, wherein each of the driving elements has a receiving circuitry connected to the second controllable switch.

9. A driver device for driving a plurality of separate capacitive load elements, the device comprising:
   first and second input terminals for connecting the driver device to a power supply;
   a plurality of output terminals each connecting the driver device to separate capacitive load elements;
   a first controllable switch connected to the first input terminal;
   a plurality of driving elements each having a second controllable switch and a resistor connected in series to each other, wherein each of the driving elements is connected in series with the first controllable switch and to the second input terminal, and wherein each of the output terminals is connected to one of the driving elements for powering the load elements,
   wherein each of the driving elements has a receiving circuitry connected to the second controllable switch,
   wherein each of the second controllable switches are connected via a third controllable switch to the second input terminal and wherein receiving circuitries are connected to a node between each of the second controllable switches and each of the third controllable switches.

10. The driver device as claimed in claim 9, comprising switch control elements adapted to switch the third controllable switches and the second controllable switches in a drive mode of the driver device in a conductive state.

11. The driver device as claimed in claim 10, wherein the switch control elements are adapted to switch the second controllable switches in a conductive state and the third controllable switches in a non-conductive state in a receive mode when the receiving circuitry is activated.

12. The driver device as claimed in claim 1, wherein the first controllable switch and the second controllable switch are integrated in one single semiconductor device.

13. The driver device as claimed in claim 1, wherein the plurality of separate capacitive elements comprise a plurality of transducer elements.

* * * * *